United States Patent [19]

Dowsett

[11] Patent Number: 5,439,921

[45] Date of Patent: Aug. 8, 1995

[54] THERAPEUTIC USE OF PIPERIDINE-2,6-DIONES

[75] Inventor: Mitchell Dowsett, Rochester, England

[73] Assignee: British Technology Group Limited, London, England

[21] Appl. No.: 960,405

[22] PCT Filed: Jul. 5, 1991

[86] PCT No.: PCT/GB91/01099

§ 371 Date: Jan. 6, 1993

§ 102(e) Date: Jan. 6, 1993

[87] PCT Pub. No.: WO92/00738

PCT Pub. Date: Jan. 23, 1992

[30] Foreign Application Priority Data

Jul. 6, 1991 [GB] United Kingdom ............... 9014968

[51] Int. Cl.⁶ .................................. H61K 31/445
[52] U.S. Cl. .................................................. 514/318
[58] Field of Search ......................................... 514/318

[56] References Cited

U.S. PATENT DOCUMENTS 3,944,671 3/1976 Dziemian et al. ................ 424/267

FOREIGN PATENT DOCUMENTS 0147121 7/1985 European Pat. Off. ............ 514/318

OTHER PUBLICATIONS

Leung, Chui-Sheung et al "Analogues of 3-Ethyl-3-(-4-pyridyl)...", J. Med. Chem. 1987, 30, pp. 1550–1553.
J. E. F. Reynolds "Martindale—The Extra Pharmacopoeia" edition 29, 1989, Pharmaceutical Press (London, GB), No. 1803, Aminoglutethimide pp. 596–598.
M. R. G. Robinson "Aminoglutethimide: Medical Adrenalectomy ..." British Jour. of Urology, vol. 52 No. 4, 1980, pp. 328–329.
Weatherall, D. J. et al (Eds) "Medical aspects of neoplasis", Oxford Textbook of Medicine, vol. 1 sections 1–12 and Index, pp. 4.143–4.145. (1987).

Primary Examiner—Goldberg: Jerome D.
Attorney, Agent, or Firm—Nixon & Vanderhye

[57] ABSTRACT

The use of compounds of formula (I)

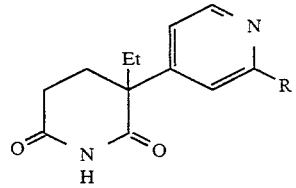

wherein R represents a hydrogen atom or an alkyl group having 1 to 4 carbon atoms and their acid addition salts, for use in the treatment of prostatic cancer or benign prostatic hypertrophy.

3 Claims, 2 Drawing Sheets

THERAPEUTIC USE OF PIPERIDINE-2,6-DIONES

This application is a continuation of PCT/GB91/01099 filed Jul. 5, 1991.

BACKGROUND OF THE INVENTION

1. Field of Invention

This invention relates to the treatment of prostatic cancer and benign prostatic hypertrophy.

2. Description of Related Art

Conditional neoplasms are those that only grow to certain specific environmental conditions. Androgen-dependent neoplasms fall into such a category, being dependent upon a source of androgens to stimulate their proliferation. Without a source of androgens, they persist but do not proliferate. It is this rationale that supports the initial approach of orchidectomy in the treatment of prostatic cancer, withdrawing the principal source of androgens. Alternatively oestrogen therapy is as effective as orchidectomy, suppressing testicular activity and therefore androgen production by inhibiting the production of pituitary gonadotrophins. There is still some proliferation of prostatic neoplasms after orchidectomy or drug-induced castration, herein collectively referred to as "therapeutic castration", this being partly due to the androgens being secreted by the adrenal gland.

Endocrine therapy, either using androgen antagonists or synthetic oestrogens as described hereinafter, is commonly practised in the treatment of prostatic cancer, both in conjunction with, and independently of therapeutic castration. Oestrogen therapy can be used as described above in depressing testicular activity, and also to treat patients who have suffered a relapse after orchidectomy, as oestrogens have shown a direct regressive effect on the carcinomas of such relapsed patients.

The major drawback in oestrogen therapy is the increased incidence of fatal thromboembolitic disease. Nevertheless, some 60% of patients obtain some relief with diethylstilboestrol, a synthetic oestrogen, a third of whom become refractory and die within two years. Flutemide and cyproterone acetate are two non-steroidal compounds that antagonize androgens; this property also offsets the feedback of androgens in the hypothalamus, stimulating an increase in the levels of luteinzing hormone (LH). The compounds are therefore not appropriate for use in non-castrate patients. Aminoglutethimide (AG) has been tried in the treatment of prostatic cancer as it blocks the side chain cleavage of cholesterol by inhibiting the enzyme desmolase. The results in a reduction of androgens, oestrogens and cortisol. A wide range of trials have been performed, the results of which indicate that some benefit s derived from the use of AG in orchidectomized patients in relapse (Chang A.Y. et al. Am. J. Clan. Oncol. 12 (4) 358–60 (1989)). The use of AG has been combined with hydrocortisone (as a cortisol replacement) but side effects such as skin rashes, lethargy and thrombocytopenia have still been observed (Elomaa I. et al. Eur. Urol. 14 (2) 104–6 (1988)). The actual mechanism through which AG is effective in the treatment of prostatic cancer is debated. Dowsett M. et al. (Br. J. Cancer 57 (2) 190–2 (1988)) do not attribute it to a lowering of adrenal androgen secretion, whereas others in this field do. Overall, the need for cortisol replacement therapy and the undesirable side effects limit the use of AG in treating prostatic cancer.

Additional prior art is referred to in a separate section after "Summary of the Invention", without which its context would not be clear.

SUMMARY OF THE INVENTION

After a trial on 10 post menopausal women with breast cancer it has been found that pyridoglutethimide (3-ethyl-3-(4-pyridyl) glutarimide), a specific aromatase inhibitor, causes a significant reduction in androgens. This was an unexpected observation as androgens are aromarase substrates and blockade of aromatase would not be expected to have an effect on androgen levels. In the light of this finding, simple derivatives of 3-ethyl-3-(4-pyridyl)glutarimide having a substituent in the pyridine ring ortho to the N-atom, would be expected to exhibit the same effect.

Accordingly the invention provides the use of compounds of the formula (I)

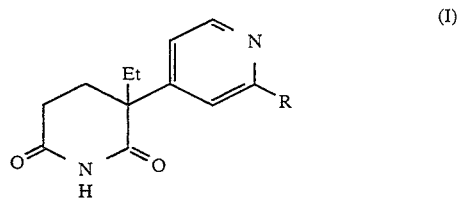

wherein R represents a hydrogen atom or an alkyl group having 1 to 4 carbon atoms (which can have a straight or branched chain in the case of propyl and butyl), and their acid addition salts, for use in the treatment of prostatic cancer and benign hypertrophy.

The compounds of formula (I) (which expression herein throughout includes the acid addition salts) are optically active. The invention includes their use in the form of their individual optical isomers and mixtures thereof, especially racemates. The R isomers are expected to show the greater activity (Boss A. M. et al. Tetrahedron 45 (18) 6011–6018 (1989)).

DESCRIPTION OF ADDITIONAL PRIOR ART

Pyrldoglutethimide (PyG) is a known aromarase inhibitor, see UK Patent No. 2,151,226 (NRDC). In that patent the properties and methods of synthesis of PyG are described as are its uses in the treatment of breast cancer. Its use in treating breast cancer is in no way suggestive of a role in the treatment of prostatic cancer as the inhibitory effect on aromarase described in the aforementioned patent does not imply that it would have any significant effect on androgen levels.

BRIEF DESCRIPTION OF THE ACCOMPANYING DRAWINGS

FIGS. 1 to 6 show the dose related effects of pyridoglutethimide on dehydroeplandrosterone sulphate (DHAS), androstenedlone, testosterone, 17-hydroxyprogesterone (17 OHP), aldosterone and cortisol respectively.

DESCRIPTION OF THE PREFERRED EMBODIMENTS

The compounds of the present invention may be prepared according to the methods described n the aforementioned UK Patent No. 2,151,226 or by a preferred method described in UK Patent No. 2,216,524 (NRDC).

The invention can be expressed as a method of treating a patient suffering from prostatic cancer or benign prostatic hypertrophy, which comprises administering to the patient a therapeutically effective dosage of a compound of formula (I) before and/or after therapeutic castration.

A preferred glutarimide derivative of formula (I) for this purpose s 3-ethyl-3-(4-pyridyl)glutarimide (pyridoglutethemide) i.e. when R is hydrogen in formula (I). The compounds of formula (I) are of use both before and after therapeutic castration but will preferably be used after castration, when the major remaining source of steroid hormones is the adrenal gland.

Benign prostatic hypertrophy is a condition exacerbated by the over-production of male steroid hormones.

A suggested range of dosage for the compounds of formula (I) in the above treatment is from at least 200 mg twice daily to at most 2000 mg twice daily.

The compounds of formula (I) can be administered to a patient in any form of composition suitable for parenteral (e.g. intravenous, intramuscular or intracavitary), oral, topical or rectal administration. Particular compositions are those in orally digestible or sterile injectable form. These forms of composition are further specified in UK Patent No. 2,151,226, the disclosure of which in this respect is herein incorporated by reference.

The following Example illustrates the invention.

EXAMPLE

EFFECT OF PYRIDOGLUTETHIMIDE (PyG) ON ADRENAL STEROID PRODUCTION

The endocrinology of post-menopausal women s comparable to that of orchidectomized men. The results of this trial are therefore indicative of the effect expected in orchidectomized men with prostatic cancer.

Ten post-menopausal patients with advanced breast cancer were treated with each of 4 sequential doses of PyG: 200 mg twice daily (b.d.), 400 mg b.d., 800 mg b.d., 1200 mg b.d. The dose changes occurred at days 14, 28 and 42, respectively. Blood samples were taken at intervals of 7 days, at least two samples being drawn before starting treatment.

Figure 1:
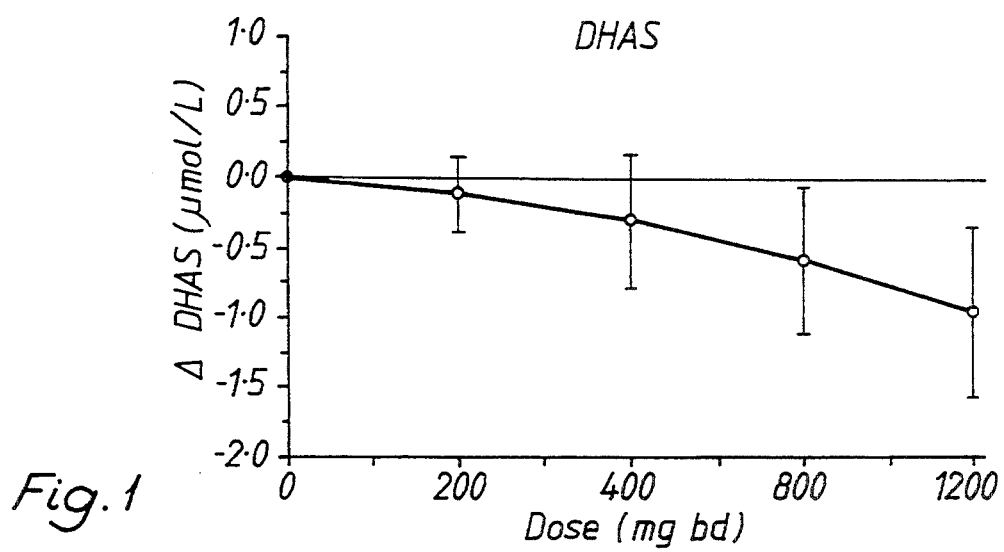
Figure 2:
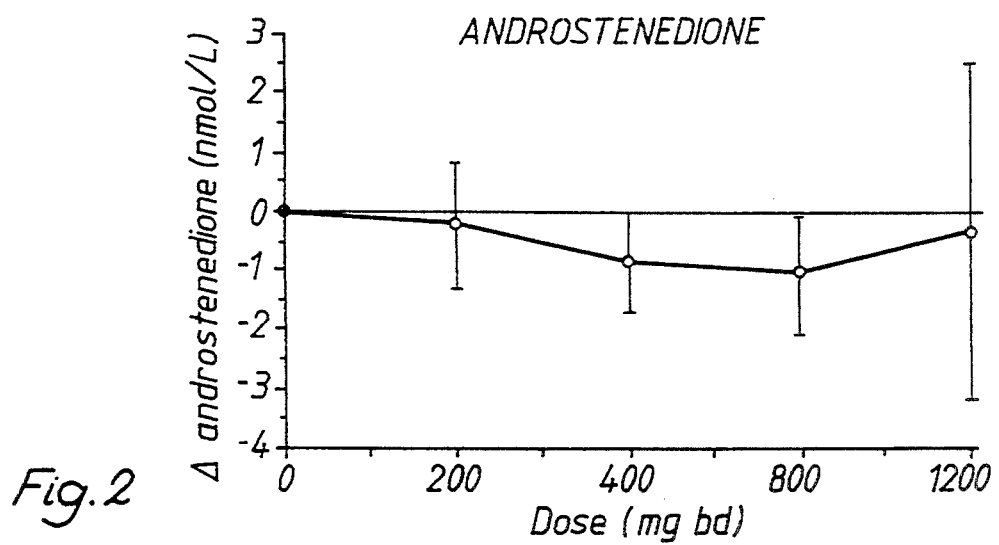
Figure 3:
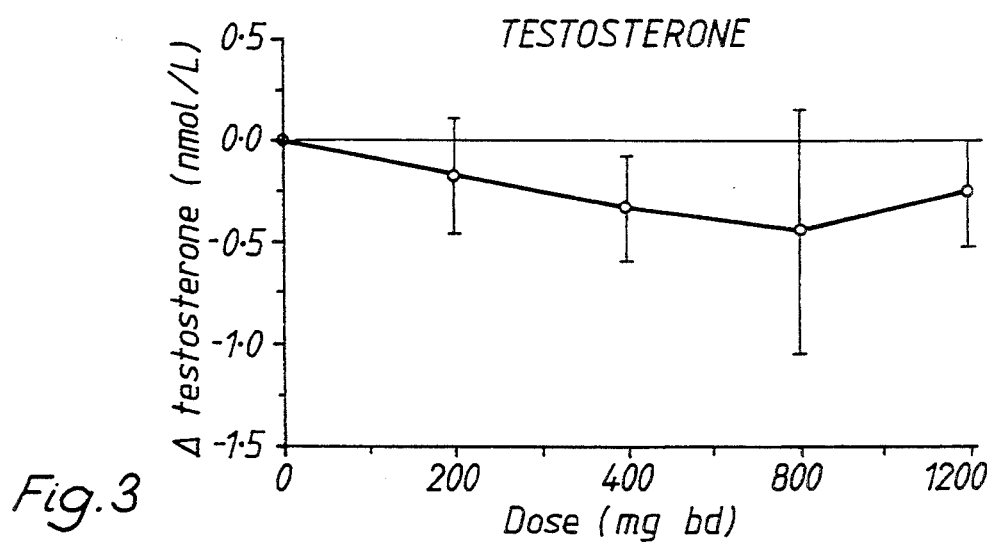
Figure 4:
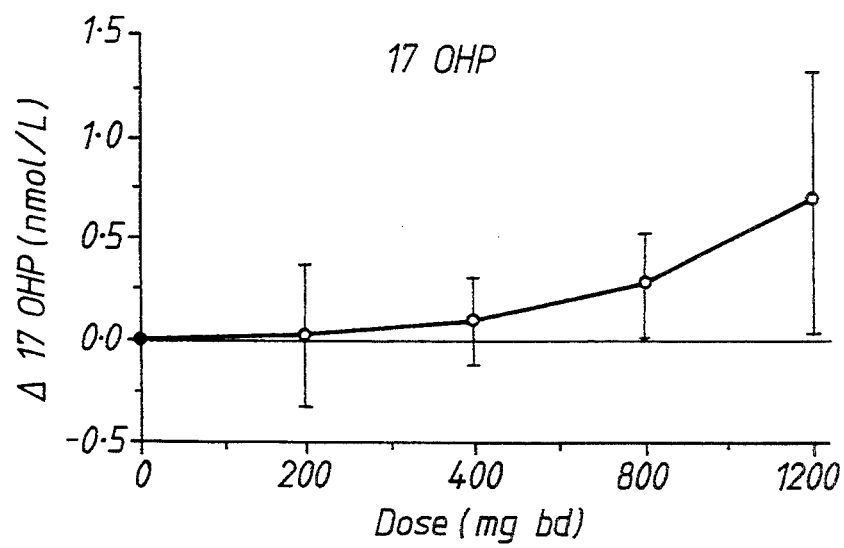
Figure 5:
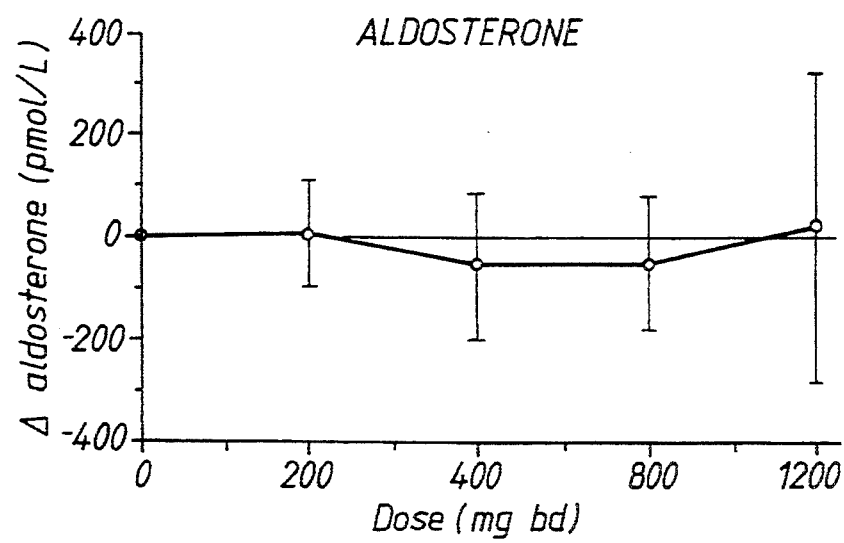
Figure 6:
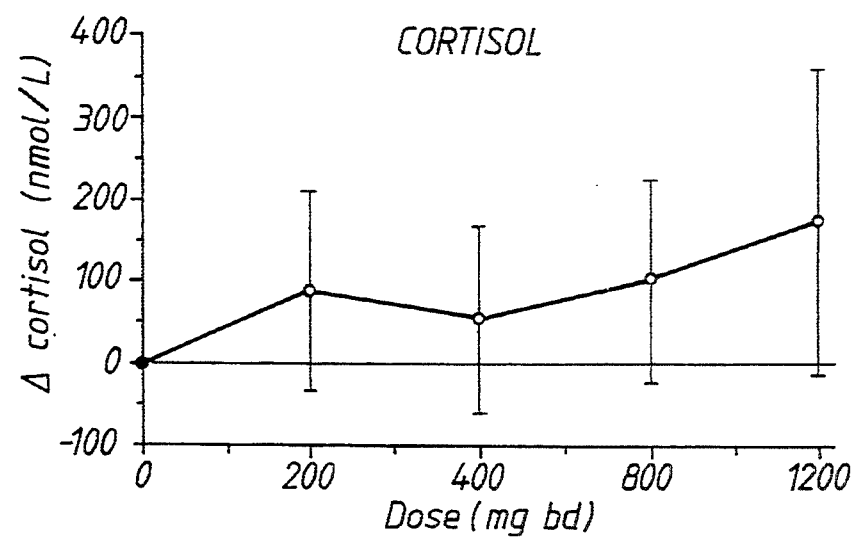

Results:

The dose-related effects of PyG on dehydroepandrosterone sulphate (DHAS), androstenedone, testosterone, 17-hydroxyprogesterone (17 OHP), aldosterone and cortisol are shown in FIGS. 1 to 6. In these Figures the results are expressed as the mean difference ±95% confidence interval of the difference. Thus, any point for which the error bar does not overlap the no change line is statistically significant at the 5% level. Some patients were withdrawn from the study before all doses were tested.

It can be seen that mean cortisol and aldosterone levels were not affected by PyG treatment. However, there was a progressive, dose-related fall of DHAS levels such that at the highest dose values were <50% of those before treatment. Both testosterone and androstenedone levels also fell and for each of these the fall was statistically significant for at least one dose. Incidentally, 17 OHP showed a (relatively minor) dose-related increase.

I claim:

1. A method of treating a patient suffering from prostatic cancer or benign prostatic hypertrophy comprising the step of administering to said patient an effective dosage of compound of formula (I)

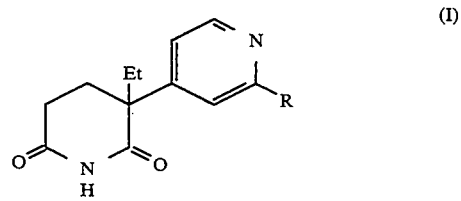

wherein R represents a hydrogen atom or alkyl group having 1 to 4 carbon atoms or an acid addition salt thereof.

2. A method according to claim 1 in which R is hydrogen.

3. A method according to claim 1 in which the dosage is from 200 to 2000 mg twice daily.

* * * * *